(12) United States Patent
Park et al.

(10) Patent No.: US 7,863,435 B2
(45) Date of Patent: Jan. 4, 2011

(54) **L-THREONINE IMPORTER FROM *CORYNEBACTERIUM* AND A PREPARATION METHOD OF A STRAIN PRODUCING L-THREONINE**

(75) Inventors: Young-Hoon Park, Seongnam-si (KR); Sang-Jo Lim, Yongin-si (KR); Seong-Jun Kim, Suwon-si (KR)

(73) Assignee: CJ Cheiljedang Corp., Seoul (KR)

( * ) Notice: Subject to any disclaimer, the term of this patent is extended or adjusted under 35 U.S.C. 154(b) by 107 days.

(21) Appl. No.: 10/582,241

(22) PCT Filed: Nov. 23, 2004

(86) PCT No.: PCT/KR2004/003031

§ 371 (c)(1), (2), (4) Date: Jun. 9, 2006

(87) PCT Pub. No.: WO2005/056800

PCT Pub. Date: Jun. 23, 2005

(65) Prior Publication Data

US 2008/0026432 A1    Jan. 31, 2008

(30) Foreign Application Priority Data

Dec. 10, 2003    (KR) .................... 10-2003-0089711

(51) Int. Cl.
*C07H 21/04*    (2006.01)
*C12N 15/77*    (2006.01)
*C12P 13/04*    (2006.01)
*A61K 31/70*    (2006.01)

(52) U.S. Cl. .................... 536/23.7; 435/487; 435/106

(58) Field of Classification Search .................... None
See application file for complete search history.

(56) References Cited

U.S. PATENT DOCUMENTS

| | | | |
|---|---|---|---|
| 6,696,561 B1 * | 2/2004 | Pompejus et al. | 536/23.7 |
| 2002/0197605 A1 * | 12/2002 | Nakagawa et al. | 435/6 |
| 2008/0026432 A1 * | 1/2008 | Park et al. | 435/115 |

OTHER PUBLICATIONS

Palmieri et al. Threonine diffusion and threonine transport in *Corynebactrium glutamicum* and their role in threonine production. Arch. Microbiol. 165:48-54, 1996 (the entire article).*
Okamoto et al. Hyperproduction of L-threonine by an *Escherichia coli* mutant with impaired L-threonine uptake. Biosci. Biotech. Biochem. 61:1877-1882, 1997.*
S. Nakagawa et al., Genbank Accession #BAC00421 Jun. 5, 2002.
J. Kalinowski et al., Genbank Accession #CAF18967, Jan. 22, 2004.
M. Ikeda et al., Appl. Microbiol. Biotechnol., vol. 62, May 2003, pp. 99-109.
J. Kalinowski et al., J. Biotechnol., vol. 104, Sep. 2003, pp. 5-25.
P. Simic et al., J. Bacteriol., vol. 183, No. 18, Sep. 2001, pp. 5317-5324.
L. Palmieri et al., Arch. Microbiol., vol. 165, 1996, pp. 48-54.

* cited by examiner

*Primary Examiner*—Quang Nguyen
(74) *Attorney, Agent, or Firm*—Birch, Stewart, Kolasch & Birch, LLP

(57) ABSTRACT

The present invention relates to a preparation method of an L-threonine producing strain by utilizing a novel L-threonine importer identified from *Corynebacterium glutamicum*. The method can be advantageously used for the production of L-threonine by increasing the fermentation concentration of Lthreonine and the yield per unit thereof.

4 Claims, 1 Drawing Sheet

SEQUENCE LISTING

<160> NUMBER OF SEQ ID NOS: 3

<210> SEQ ID NO 1
<211> LENGTH: 4846
<212> TYPE: DNA
<213> ORGANISM: Corynebacterium glutamicum ATCC 13032

```
<220> FEATURE:
<221> NAME/KEY: gene
<222> LOCATION: (23)..(1168)
<223> OTHER INFORMATION: ORF1
<220> FEATURE:
<221> NAME/KEY: gene
<222> LOCATION: (1772)..(3025)
<223> OTHER INFORMATION: ORF2, novel L-threonine importer (thrY)

<400> SEQUENCE: 1
```

| | | | | | |
|---|---|---|---|---|---|
| gatcggtccg | cacggctggc | gaatgctgga | atcctggggt | ctgctcgacc | aaattgtcgt | 60 |
| ggccggctac | ctcccagaag | acatgcagtt | ccgcgacgct | gtcaaccgcg | aaaccatcct | 120 |
| gaccatgcgt | ttcgatgaag | aattccagca | gcactacggc | ggtcgctacc | tggtgattca | 180 |
| ccgctctgac | ctgctcaaca | tcctggtcac | caacgccgaa | gcagcgggcg | cgaagctcca | 240 |
| caatggcgtc | ctggtcaccg | attcccgcac | cgtcgacggc | ggtatcgagg | tggacatcga | 300 |
| atcctccatc | aacaagggcg | aagataacaa | gactttgctt | gtcgacgcct | tcctcgcctt | 360 |
| cgacggcatc | cactcggtca | tgcgcaaaaa | gcttgtcgac | gacgccccg | tcgcctcctc | 420 |
| ctacgtcgcc | taccgcggca | cctccaagct | ggcagaagac | gccgaaatga | aggacctgaa | 480 |
| atccgtcatc | ggctacatcg | gaccacacgt | gcacttcatc | caatacccac | tgcgcggcgg | 540 |
| agaactcctc | aatcaggtcg | ccgtctttga | atcccagcgt | tacctcgatg | gacgcaccgc | 600 |
| cggcgacatc | ccagaagact | ggggcaaccc | cgaagaatta | gaccgcgcct | acaaccactg | 660 |
| cgaccccttc | atccaggacc | gtctggacac | cctgtggcgc | aacaactggt | ggcaaatgtc | 720 |
| cgaccgcgag | cctctagaga | actggcgtat | cggccgcatg | ttgctgcttg | gcgacgccgc | 780 |
| ccacgcaccc | ctccagtacc | tcgcctcagg | cgcggtcatg | gccatggaag | acgccgaggc | 840 |
| tgtcgccctc | ttcgctgccg | acgctgcgcg | tgctggcaac | ctcgattggg | aagaggtact | 900 |
| cgcagaggtg | gaagctgaac | gccgaccacg | ctgcagccgc | atccaaaccg | taggccgttt | 960 |
| ctggggagag | ctctggcatg | tggaaggcac | cgcacgtctc | atccgcaacg | aagtttttccg | 1020 |
| ccaagcagac | cgcaatggct | ggttcatcta | tgcagactgg | ctgtgggggtt | acgatgcatc | 1080 |
| caagcgtgcc | cacatcgcca | accctgagct | cggagaaatg | ccacaagcac | tgaaggaatg | 1140 |
| gcgctacgcc | ctcctcgaac | agaaatagca | gcctcacctg | ttaagggaaa | attgtgtgct | 1200 |
| tttcccaggc | aggctcttta | atgtcgagtt | cttaagttcg | atttcttaac | agcgatttca | 1260 |
| gtcggaaaac | cggggaaaac | cgagcgaaat | cgctgttgag | aaattgagct | tgaggtattg | 1320 |
| gaaccatgaa | ctcgacaccg | tgaaatcgca | gttaagaaac | aaccgcgaaa | tatgggcgtt | 1380 |
| taaggcgtcg | aggtttccgt | atgggtgtga | gtctagggag | agccagttaa | ggcccttaga | 1440 |
| agcgattctg | tgaggtcaaa | cttttaggga | tctcggtcgt | gaattcaccc | ttttcgaggc | 1500 |
| agaccagaca | ggcgtgacaa | gattggcgaa | aaagccgagg | ttttggcacg | tgtgtccggt | 1560 |
| ttccaatccc | ctaaaccaga | cagacgtgcc | aaaacctggc | gaaaatccag | attcttgtca | 1620 |
| cgcctgtctg | gtttctcctt | ttgagcgacc | caaaccacgc | ccgaaccacc | gttccacagc | 1680 |
| ccccacgaac | cctcaagaca | gaaaagatcg | caccagccgc | atcgagctgg | tgcgatcaaa | 1740 |
| ccgcagtaaa | aactacagaa | aatgcgggtt | tctacttgtg | atgttccaca | tccgatggag | 1800 |
| tgatgtcgaa | ggcaacgcgg | tcgtcttctt | cgatttcatc | tggggaagtg | gtgtgcagct | 1860 |
| ggccccttgg | gaatttgttc | acgatgactg | cgattgcgcc | gtcgccggtg | acgtttgctg | 1920 |
| cggtgccgaa | ggagtcaatc | gcgatgtaag | cggcgatcat | gagggcgact | tgttcggtgt | 1980 |
| tgaatccgag | catggaggcc | agcatgccgg | ttgctgccat | gatggctccg | ccgggaacgc | 2040 |

-continued

```
ctggtgcggc gatcatggtg atgcccagca tgaggaggaa tccgatggag aggccgacgc   2100
ctacttccat gtcgtacatg aagacaacag cgaaggtgaa gaggccgatc ttcatcatcg   2160
atccagctag gtggatggtg gcgcacagtg ggacaacaaa gcctgcgacg ttgacatcaa   2220
catcgttttt cagggtctgc tggtaggtca ctggatggt tgccgctgaa gaggaggtgc   2280
ccagtgcagt gaagtatgca gggagcatgt ttttgaacag tttccatggg ttcttcttgg   2340
atactgcacc agcgataatg aactggatgg ctaggaagag cagggttccc acgacggcga   2400
gaatcagtac cttgccaaag gcggacatga tctccaggag gccaccgttc atgcccatgc   2460
cgaggaagat gccgaagatg aagagtggca gcagtgggat gacaaaggcg gtgatggtct   2520
tcatgactac gcgctcgagt tcgcgggtta ccttgaacag ggtgtctgat ttaattacag   2580
ccatgcccag gccgaggcag aatgccagca gcagtgcggt catcacttca aatggtggtg   2640
gcatctcgat gttgaagtag ggctggaggg cacctgcatc aaggtcgatt tcggtgacgc   2700
tttggtggtc tttcagcagc catgggtaga gcgcttggga tgctccgtag gcgatcagac   2760
cggagaagac ggtggacgcg taggcgattg ctgcaacaat gccgagccat tgccagcgc   2820
ctcggccgag ccctgcaatg gcgggggcga tgagggagaa gatcagcact gggatgaaga   2880
agcccagaaa gttgctgaat aggccgttga aggtggtgaa gatctcagcg agccacaccg   2940
ggaagaagag gctgcagatg attccgagga tgatggcaac gatcactcgg aacagcagcg   3000
acgagctcat gctctttatg tccatggttg ttccttattt ctaatcaggt gctgtctgag   3060
caatgctcgg cagcgcgtga tggaattttg tgtgcggctt ggaagtgacg ggtcacaagg   3120
acagctcgtg tagaccctgc ctggagcctt gacaaactcc accaaacaac tgcgacgtgt   3180
gtcagattac tgcaggcttg tggtcaaacc tagttctttg gaggcggagc atcatacctt   3240
ttaatgtcag gatcgtgcag tgaagaattc aggatgaatt actcgctgga atattggtgg   3300
ggatagagtt gttgttatga cggtgatcgg aattattctt ggcagccttt ttggcgttct   3360
tgcagtcctt ctcatcgtgg ttggtgcttt ggggtgggcg gctaagctcc ctggcaaccc   3420
ggttgtgggc attcgtgtcc ctgaggtgcg taaatcccaa gaattgtggg atatggcgca   3480
ccgtgtcgct ggcccgttgt gggtgctgtc gggagtttcc tttgttattg catcgctagt   3540
tgcgtttgtt gcttctggtt ggatgtggct tgttgtggcg ttgggtgttg tggctgccat   3600
cgtgttcatt ggtatgggtg cgggtatggc tgcgcatact gttgcgatgg ttgacgcgaa   3660
gcgcagtcgc gaaacccgc aggcgcctgt ttccgctgaa attgaagagg ccggtggtgt   3720
gactattacc tcgccgatta tcaacaagac tccgctgaat gccccaaga ttgacttgga   3780
tgcagtgcgt agagctgcgg aaactacgca agaacccaaa aatgattaat aattgagaca   3840
agcttcccac tatgtgataa agtcccattt tgtgaataac tcttgtctca gtcaaagcac   3900
ccagtggtgg tggcgcgcta actaagcgag cctgacacct caagttgttt tcactttgat   3960
gaatttttta aggctcgtac ttcgttcgac gaagaagcgg gccttttgtg gttttagcc    4020
cacaaccggc aagccctgga tcgaatgaag ctcgcagcga gtaattattt gatgtttccc   4080
agaaaggctt cagcccccaca atgatttcct cggtaggtgc cccatgagca cgaatccca    4140
tgttttctcc ctagatgtcc gctatcacga ggatgcttct gcattgtttg cccacttggg   4200
tggcacaacc gcagatgatg cagccctgtt ggaaagcgct gatatcacca ccaagaatgg   4260
tatttcttcc ctcgcggtgt tgaagagttc ggtgcgcatt acgtgcacgg caacacggt    4320
ggtaacgcag ccgctgacgg actcgggtag ggcagtggtt gcgcgcctaa cgcagcagct   4380
tggccagtac aacaccgcag agaacacctt tagcttcccc gcctcagatg cggttgatga   4440
```

-continued

```
gcgcgagcgc ctcaccgcac caagcaccat cgaagtgctg cgcaagttgc agttcgagtc    4500
cggctacagc gacgcgtccc tgccactgct catgggcggt ttcgcgtttg atttcttaga    4560
aacctttgaa acgctccccg ctgtcgagga gagcgtcaac acttaccccg attaccagtt    4620
cgtcctcgcg gaaatcgtcc tggacatcaa tcaccaggac cagaccgcca aactcgccgg    4680
cgtctccaac gccccaggcg agctcgaggc cgagctcaac aagctttcat tgcttatcga    4740
cgccgccctc cccgcaaccg aacacgccta ccaaaccacc cctcacgacg gcgacactct    4800
tcgcgttgtg gctgatattc ccgatgctca gttccgcacc cagatc                  4846

<210> SEQ ID NO 2
<211> LENGTH: 25
<212> TYPE: DNA
<213> ORGANISM: Artificial Sequence
<220> FEATURE:
<223> OTHER INFORMATION: Synthetic PCR primer

<400> SEQUENCE: 2
gacttgttcg gtgttgaatc cgagc                                           25

<210> SEQ ID NO 3
<211> LENGTH: 25
<212> TYPE: DNA
<213> ORGANISM: Artificial Sequence
<220> FEATURE:
<223> OTHER INFORMATION: Synthetic PCR primer

<400> SEQUENCE: 3
cggtctgatc gcctacggag caatc                                           25
```

L-THREONINE IMPORTER FROM *CORYNEBACTERIUM* AND A PREPARATION METHOD OF A STRAIN PRODUCING L-THREONINE

TECHNICAL FIELD

The present invention relates to a preparation method of an L-threonine producing strain by utilizing a novel L-threonine importer identified from *Corynebacterium glutamicum*.

BACKGROUND ART

Traditional preparation methods of an amino acid-producing strain include increasing the amount of a gene expressed on the biosynthetic pathway of an objective amino acid, releasing feedback inhibition and transcription inhibition by an object project, and increasing the supply of precursor by intensifying a gene on the central metabolic pathway. In other words, the traditional breeding method was focused mainly on the cultivation of a strain whose synthesis is not easily inhibited by an excessive production of objective amino acid in a cell.

In recent years, however, active studies have been performed on various amino acid importers/exporters for use in the preparation of an amino acid-producing strain. The studies are aimed to protect many enzymes on the biosynthetic pathway from the feedback inhibition and the transcription inhibition by an object product. This is made it possible by reducing the concentration of a particular amino acid in a cell through the importer defect or the intensification of the exporter of that particular amino acid. For instance, the report on lysine exporter (lysE) of *Corynebacterium glutamicum* (*Microbiology*, 147:1765, 2001), and the report on the threonine production improvement by expressing threonine exporter (thrE) of *Corynebacterium glutamicum* from *E. coli* (*Appl. Microbiol. Biotechnol.*, 59:205, 2002) are some of the examples of the intensification of the exporter to increase the yield of a specific amino acid. As mentioned the above, the importer of a specific amino acid can also be defected to increase the yield of the amino acid. For example, the yield of tryptophan was increased by a mutant strain defective in the importer of an aromatic amino acid of *Corynebacterium glutamicum* (*Biosci, Botech. Biochem.*, 59:1600, 1995), and a strain defective in the threonine importer was prepared from *E. coli* to increase the yield of threonine (*Biosci. Botech. Biochem.*, 61:1877, 1997).

In this light, the present inventors have tried to prepare a threonine-producing strain from *Corynebacterium glutamicum* based on the discovery that the concentration of intracellular threonine was reduced and the feedback inhibition and the transcription inhibition by threonine of a threonine biosynthetic gene could be prevented by blocking transfection of threonine of high concentration into a cell, which was made it possible by defecting the threonine import pathway. That is, a threonine importer was identified and defected to produce the threonine-producing strain from *Corynebacterium glutamicum*.

DESCRIPTION OF THE DRAWINGS

The above and other objects, features and other advantages of the present invention will be more clearly understood from the following detailed description taken in conjunction with the accompanying drawings, in which.

DISCLOSURE

Technical Problem

Figure 1:
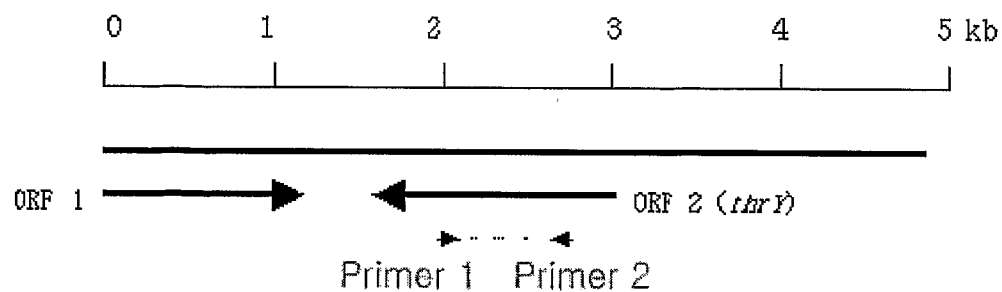
FIG. 1 illustrates a gene arrangement in a cloned DNA fragment.

Therefore, the present invention has been made in view of the above problems, and it is an object of the present invention to identify a novel L-threonine importer from *Corynebacterium glutamicum*.

It is another object of the present invention to provide a preparation method of an L-threonine producing strain defective in the importer and thus, to increase the yield of L-threonine.

Technical Solution

In accordance with an aspect of the present invention, the above and other objects can be accomplished by cloning and identifying a novel L-threonine importer from a wild *Corynebacterium glutamicum* strain.

In accordance with another aspect of the present invention, there is provided a preparation method of a strain defective in L-threonine importer of *Corynebacterium glutamicum*, thereby increasing the yield of L-threonine.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

ADVANTAGEOUS EFFECTS

Therefore, the present invention can be advantageously used for preparing a threonine-producing strain from *Corynebacterium glutamicum*.

BEST MODE FOR INVENTION

A threonine importer-defective strain was prepared from *Corynebacterium glutamicum*, in which the defective strain was used as a host strain for cloning a threonine importer.

To this end, the present inventors decided to prepare a high-threonine-requiring strain from a low-threonine-requiring strain. This was based on the assumption that if the threonine importer of the low-threonine-requiring strain was defective, it might be possible to obtain a high-threonine-requiring character. Therefore, the high-threonine-requiring strain prepared from the low-threonine-requiring strain would be the threonine importer-defective strain.

To prepare the strain, *Corynebacterium glutamicum* CJ L-1, the threonine auxotrophic strain prepared by using *Corynebacterium glutamicum* ATCC 13032, was used as a parent strain. The CJ L-1 strain demonstrated 20 mg/l of auxotrophy with respect to threonine. The high-threonine-requiring strain, namely *Corynebacterium glutamicum* CJ L-11 strain, manifesting 500 mg/l of auxotrophy was prepared from the CJ L-1 strain through artificial mutation. By using the CJ L-11 strain as a host strain, the genomic library of ATCC 13032 (which is the wild strain of *Corynebacterium glutamicum*) went through transformation and as a result, a low-threonine-requiring clone was obtained.

Thusly obtained clone was retransformed to the high-threonine-requiring strain to make sure that the concentration of threonine in the strain is low. Afterwards, DNA base sequence was analyzed to check which genes were contained in the cloned DNA fragment. It was discovered that the cloned DNA fragment contained 4,846 bases. Then the open reading frame (ORF) of the gene in the DNA fragment was searched again by means of the ORF Finder. In result, a predominant membrane protein gene of 1,254 bp (% length) was searched.

Homologous genes thereof were then searched by means of BLASTP, and it turned out that the gene manifested 48% of homology with serine/threonine transporter of *Porphyromonas gingivalis*, and 51% of homology with Na$^+$/H$^+$-dicarboxylate symporter of *Bacterioides thetaiotaomicron*. According to the report by Eikmanns et. al. (*Arch. Microbiol.*, 165:48, 1996), as far as *Corynebacterium glutamicum* is concerned threonine and Na$^+$ are introduced into a cell at the same time, and threonine and serine are imported by a common importer. Based on these known facts, the present inventors assumed that the gene product of the cloned membrane protein in the DNA fragment could be the threonine importer, and named the gene product thrY.

To verify the assumption, the present inventors destroyed the gene in question of *Corynebacterium glutamicum* CJ L-1 strain (which is the low-threonine-requiring strain), in order to check if the low-threonine-requiring strain was transformed to the high-threonine-requiring strain. To prepare a defective strain, only the central part of the protein coding region of the gene went through DNA Polymerase Chain Reaction (PCR) and was cloned to an *E. coli* vector. The same was transformed to *Corynebacterium glutamicum* CJ L-1 strain, which is the low-threonine-requiring strain, and a single cross-over movement was performed thereon to get the defective strain. The same method was employed to prepare a thrY defective strain from *Corynebacterium glutamicum* CJ L-1 strain which is the low-threonine-requiring strain. It was found out that thrY defective strain manifested 300 mg/l of high threonine auxotrophy. Based on these discoveries, it was concluded that the cloned thrY was indeed the threonine importer.

Further, the present inventors wanted to find out what happens to the yield of threonine when thrY of the threonine-producing strain of *Corynebacterium glutamicum* was really destroyed. For this experiment, CJ T-2, the threonine-producing *Corynebacterium glutamicum* recombination strain, was selected as a target strain, and the above-described method was used to defect the gene. Thusly prepared gene defective strain was named CJ T-21, and the same was actually used to produce threonine. It turned out that the yield of threonine was increased by 10% compared with the case where the parent strain thrI was used.

EXAMPLE 1

Preparation of High-Threonine-Requiring Strain from *Corynebacterium glutamicum*

A threonine importer-defective strain was prepared from *Corynebacterium glutamicum*, in order to use the defective strain as a host strain for cloning a threonine importer. To this end, a high-threonine-requiring strain was prepared from a low-threonine-requiring strain.

To prepare the high-threonine-requiring strain, *Corynebacterium glutamicum* CJ L-1, which is the threonine auxotrophic strain prepared by using *Corynebacterium glutamicum* ATCC 13032, was used as a parent strain. The CJ L-1 strain manifested 20 mg/l of auxotrophy with respect to threonine. The CJ L-1 strain went through the artificial mutation process to produce the high-threonine-requiring strain. To induce the artificial mutation, N-methyl-N'-nitro-N-nitrosoguanidine (NTG), one of alkylating agents, was used. *Corynebacterium glutamicum* CJ L-1 grew in Luria-Bertani liquid medium until the mid of the logarithmic growth phase, and was suspended in citrate buffer (pH 5.5) to $10^7 \sim 10^8$ cells/ml. When the final concentration of the NTG became 1,000 μg/ml, the CJ L-1 strain was placed in the concussor (or the shaker) at 30° C. for 5 minutes. Later the strain was washed by potassium phosphate (pH 7.0) three times, and smeared over a minimal medium containing 2,000 mg/l of threonine. Approximately 30,000 colonies grown in the medium were subject to the tooth picking process in the presence of the minimal medium containing 20 mg/l of threonine, and any strains that were not grown were selected. These selected strains were checked again if they have the threonine-requiring character. A 500 mg/l-threonine-requiring strain was finally selected and named *Corynebacterium glutamicum* CJ L-11. The CJ L-11 was then used as a host strain for cloning the threonine importer.

TABLE 1

| Minimal agar medium | | | |
|---|---|---|---|
| Ingredient | Content | Ingredient | Content |
| Glucose | 10 g | CaCl$_2$2H$_2$O | 0.1 g |
| (NH$_4$)$_2$SO$_4$ | 2 g | Na$_2$B$_4$O$_7$10H$_2$O | 80 μg |
| Urea | 2 g | (NH$_4$)$_6$MoO$_2$7$_4$H$_2$O | 40 μg |
| KH$_2$PO$_4$ | 3.0 g | ZnSO$_4$7H$_2$O | 10 μg |
| MgSO$_4$7H$_2$O | 0.5 g | CuSO47H$_2$O | 300 μg |
| FeSO$_4$7H$_2$O | 10 mg | MnCl$_2$4H$_2$O | 10 μg |
| MnSO$_4$5H$_2$O | 10 mg | FeCl$_3$6H$_2$O | 1 mg |
| Biotin | 100 μg | Agar | 20 g |
| Thiamine HCl | 100 μg | Distilled water | Per liter |
| pH (prior to disinfection) 7.0 | | | |

EXAMPLE 2

Cloning of Threonine Importer

The *Corynebacterium glutamicum* CJ L-11, the high-threonine-requiring strain, prepared in Example 1 was used as a host strain to clone a threonine importer from ATCC 13032, the *Corynebacterium glutamicum* wild strain.

To this end, a chromosome library of *Corynebacterium glutamicum* ATCC 13032 was constructed and transformed to the *Corynebacterium glutamicum* CJ L-11, in order to obtain a low-threonine-requiring clone.

For the construction of the chromosome library, *Corynebacterium glutamicum* ATCC 13032 strain was cultured in Luria-Bertani medium for 16 hours to prepare a seed culture medium. 1% of the seed culture medium was then seeded in 10 ml of Luria-Bertani medium containing 1% of glycine, and the strain was cultured therein for 12 hours. A mycobiant was collected from the cultured strain, and a chromosomal DNA was separated from the mycobiant by means of the Genomic DNA Kit manufactured by Qiangen Company. Later, 2 μg of the chromosomal DNA was mixed with Sau3A1 restriction enzyme 0.1 unit and cultured for 1 hour at 37° C. to be partially cut off. This partially-cut chromosomal DNA was purified by 0.8% agarose gel electrophoresis into DNA fragments of 4-6 kb. Finally, the gel-purified DNA fragment was introduced to the position of BamHI restriction enzyme of pECCG122 which is the *Corynebacterium* vector, to complete the chromosome library.

The chromosome library was then transformed to the *Corynebacterium glutamicum* CJ L-11 (which is the high-threonine-requiring strain), and smeared over the minimal medium containing 20 mg/l of threonine. Afterwards, a plasmid DNA was extracted from colonies produced in the medium and retransformed to the *Corynebacterium glutamicum* CJ L-11. Finally, a clone that recovered the low-threonine-requiring character from the high-threonine-requiring character was selected and named pECCG-thrY.

EXAMPLE 3

Base Sequence Analysis of Cloned DNA Fragment

To check the genes in the low-threonine-requiring clone obtained in Example 2, appropriate primers were synthesized and went through DNA sequencing to be overlapped. In this manner the base sequence of the cloned DNA fragment was determined (please refer to the SEQ. ID No. 1).

It turned out that the cloned DNA fragment was composed of 4,846 bases. Then the open reading frame (ORF) of the gene in the DNA fragment was searched again by utilizing the ORF Finder. In result, two ORF of longer than 1 kb were searched. More specifically, the ORF1 (i.e., the SEQ. ID No. 1) was a 1,146 bp gene from the $23^{rd}$ base to the $1,168^{th}$ base, and the other ORF2 was a 1,254 bp gene from the $1,772^{nd}$ base to the $3,025^{th}$ base (please refer to FIG. 1).

Homologous genes thereof were then searched by means of BLASTP. It turned out that the ORF1 manifested high homology with genes such as hydroxylase or monooxygenase of various microorganisms. Meanwhile, the ORF2 manifested 48% of homology with serine/threonine transporter of *Porphyromonas gingivalis*, and 51% of homology with $Na^+/H^+$-dicarboxylate symporter of *Bacterioides thetaiotaomicron*.

According to a published report, as far as *Corynebacterium glutamicum* is concerned threonine and $Na^+$ are introduced into a cell at the same time, and threonine and serine are imported by a common importer. Based on these known facts, the present inventors assumed that the gene product of the cloned membrane protein in the DNA fragment could be the threonine importer, and named the gene product thrY.

EXAMPLE 4

Preparation of thrY-defective Strain from Low-Threonine-Requiring Strain CJ L-1 and Characteristics Thereof To confirm the involvement of the cloned thrY in the threonine import, the present inventors destroyed the gene in question of *Corynebacterium glutamicum* CJ L-1 strain (which is the low-threonine-requiring strain), in order to check if the low-threonine-requiring strain was transformed to the high-threonine-requiring strain.

Figure 2:
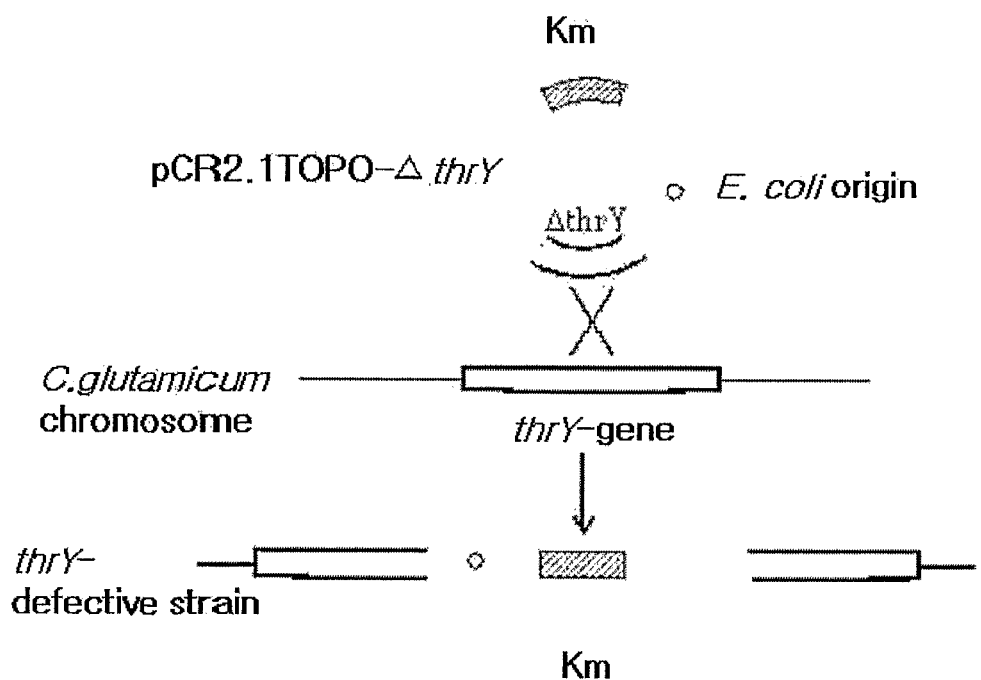
FIG. 2 illustrates a gene deficit caused by a single cross-over using an *E. coli* vector.

To prepare the thrY-defective strain, only the central part of the protein coding region of the gene went through DNA Polymerase Chain Reaction (i.e., primer 1: 5'-GACTTGT-TCGGTGTTGAATCCGAGC-3', (SEQ ID NO: 2) primer 2: 5'-CGGTCTGAT CGCCTACGGAGCAATC-3' (SEQ ID NO: 3)) and was cloned to an *E. coli* vector such as pCR2.1-TOPO (which is produced by Invitrogen Company). The same was transformed to *Corynebacterium glutamicum* CJ L-1 strain, which is the low-threonine-requiring strain, and a single cross-over movement was performed thereon to get the defective strain (please refer to FIG. 1 and FIG. 2). Later, it was found out that the threonine auxotrophy of thrY defective strain was markedly increased from 20 mg/l to 300 mg/l.

Based on these discoveries, the present inventors concluded that the cloned thrY was indeed the threonine importer.

EXAMPLE 5

Preparation of thrY-Defective Strain from Threonine-Producing Strain and Production Experiment of Threonine To find out how the destruction of thrY of the threonine-producing strain affects the yield of threonine, the present inventors conducted the following experiment.

For the experiment, CJ T-2, the threonine-producing *Corynebacterium glutamicum* recombination strain, was selected as a target strain, and the above-described method was used to defect the gene. Thusly prepared gene defective strain was named CJ T-21, and the same was actually used to produce threonine.

As for the fermentation, the strain was placed in a 250 ml baffle flask (culture medium: 25 ml) and cultured in a concussor (or a shaker) at 30° C. and 230 rpm for 72 hours. The composition of the fermentation medium is illustrated in the following Table 2. After measuring the concentration of threonine, the present inventors discovered that the parent strain accumulated 7.3 g/l of threonine in the culture medium, and the thrI defective strain accumulated 8.1 g/l of threonine, showing approximately 10% of increase. This is because threonine import into a cell was basically blocked because of the defective thrY, so the concentration of threonine in the cell was reduced. Accordingly, threonine biosynthetic genes could avoid the feedback inhibition or the transcription inhibition by threonine.

TABLE 2

| Flask fermentation medium | |
|---|---|
| Ingredient | Content |
| Molasses (reducing sugar) | 100 g |
| Yeast concentrated extract | 4 g |
| $(NH_4)_2SO_4$ | 40 g |
| Urea | 4 g |
| $KH_2PO_4$ | 1 g |
| NaCl | 2.5 g |
| $MgSO_4 7H_2O$ | 0.5 g |
| $FeSO_4 7H_2O$ | 10 mg |
| $MnSO_4 5H_2O$ | 10 mg |
| Biotin | 100 µg |
| Thiamine HCl | 200 µg |
| $CaCO_4$ | 40 g |
| Process water | Per liter |
| pH (after disinfection) | 7.0 |

The invention claimed is:

1. An isolated DNA molecule encoding a threonine importer, wherein said DNA molecule consists of continuous nucleotides 1,772 to 3,025 of SEQ. ID. No. 1.

2. A method for increasing the yield of threonine produced by a threonine-producing *Corynebacterium* strain comprising:
   (a) inactivating an endogenous threonine importer gene of the threonine-producing *Corynebacterium* strain, wherein the threonine importer gene comprises continuous nucleotides 1,772 to 3,025 of SEQ. ID. No. 1, and
   (b) culturing the threonine-producing *Corynebacterium* strain of step (a) under suitable conditions, and thereby increasing the yield of threonine produced by the threonine-producing *Corynebacterium* strain in a fermentation medium.

3. A threonine-producing *Corynebacterium* strain comprising an inactivated endogenous threonine importer gene, wherein the endogenous said threonine importer gene prior to inactivation comprising continuous nucleotides 1,772 to 3,025 of SEQ. ID. No. 1.

4. The method of claim 2, wherein the *Corynebacterium* strain is a *Corynebacterium glutamicum* strain.

* * * * *